US00PP35548P2

(12) United States Plant Patent
Wu et al.

(10) Patent No.: US PP35,548 P2
(45) Date of Patent: Dec. 12, 2023

(54) BERMUDAGRASS CULTIVAR 'OKC1876'

(50) Latin Name: ***Cynodon transvaalensis* x *Cynodon dactylon* var. *dactylon***
Varietal Denomination: OKC1876

(71) Applicant: THE BOARD OF REGENTS FOR THE OKLAHOMA AGRICULTURAL AND MECHANICAL COLLEGES, Stillwater, OK (US)

(72) Inventors: Yanqi Wu, Stillwater, OK (US); Dennis Loren Martin, Stillwater, OK (US); Justin Q. Moss, Stillwater, OK (US); Charles H. Fontanier, Stillwater, OK (US)

(73) Assignee: THE BOARD OF REGENTS FOR THE OKLAHOMA AGRICULTURAL AND MECHANICAL COLLEGES, Stillwater, OK (US)

( * ) Notice: Subject to any disclaimer, the term of this patent is extended or adjusted under 35 U.S.C. 154(b) by 0 days.

(21) Appl. No.: 17/803,803

(22) Filed: Nov. 29, 2022

(51) Int. Cl.
*A01H 5/12* (2018.01)
*A01H 6/46* (2018.01)

(52) U.S. Cl.
USPC ..... Plt./389

(58) Field of Classification Search
USPC ..... Plt./389
CPC ... A01H 5/12; A01H 5/00; A01H 5/02; A01H 6/46; A01H 6/4612
See application file for complete search history.

(56) References Cited

U.S. PATENT DOCUMENTS

| | | | |
|---|---|---|---|
| PP11,181 | P | 1/2000 | Riley |
| PP18,247 | P3 | 11/2007 | Parsons et al. |
| PP24,116 | P3 | 12/2013 | Wu et al. |
| PP27,392 | P2 | 11/2016 | Hanna et al. |
| 2012/0304349 | P1 | 11/2012 | Wu et al. |
| 2019/0364715 | P1 | 11/2019 | Wu et al. |

*Primary Examiner* — June Hwu
(74) *Attorney, Agent, or Firm* — McKee, Voorhees & Sease, PLC

(57) ABSTRACT

'OKC1876' is disclosed herein as a new clonally propagated F1 hybrid Bermudagrass cultivar with improved drought resistance, excellent fall color retention, reduced seedheads, and high turfgrass quality.

3 Drawing Sheets

GOVERNMENT SUPPORT

This invention was made in part with government support under United States Department of Agriculture SCRI Grant Nos. SCRI-2015-51181-24291 and SCRI-2019-1455-15/2019-51181-30472. The government has certain rights in this invention.

Botanical designation:

Genus and species: *Cynodon transvaalensis* x *Cynodon dactylon* var. *dactylon.*

Cultivar denomination: The new plant has the cultivar denomination 'OKC1876'.

SUMMARY

This disclosure relates to a new and distinct cultivar of bermudagrass designated 'OKC1876' and botanically known as *C. transvaalensis* Burtt-Davy x *C. dactylon* Persoon. 'OKC1876' is a turf-type, clonally propagated, F1 bermudagrass hybrid characterized by improved drought resistance, extended late-season color retention, high turfgrass quality, excellent establishment characteristics, sufficient traffic tolerance, and sod tensile strength.

DETAILED BOTANICAL DESCRIPTION

The following is a detailed botanical description of the new cultivar of bermudagrass, its flowers, foliage etc. as based on two years of continuous observations of specimens grown in field conditions in various locations throughout Virgina, Indiana, Arkansas, Kansas, Missouri, Oklahoma, New Mexico, Florida, Tennessee, Kentucky, Alabama, and Mississippi.

Origin and History

Figure 1:
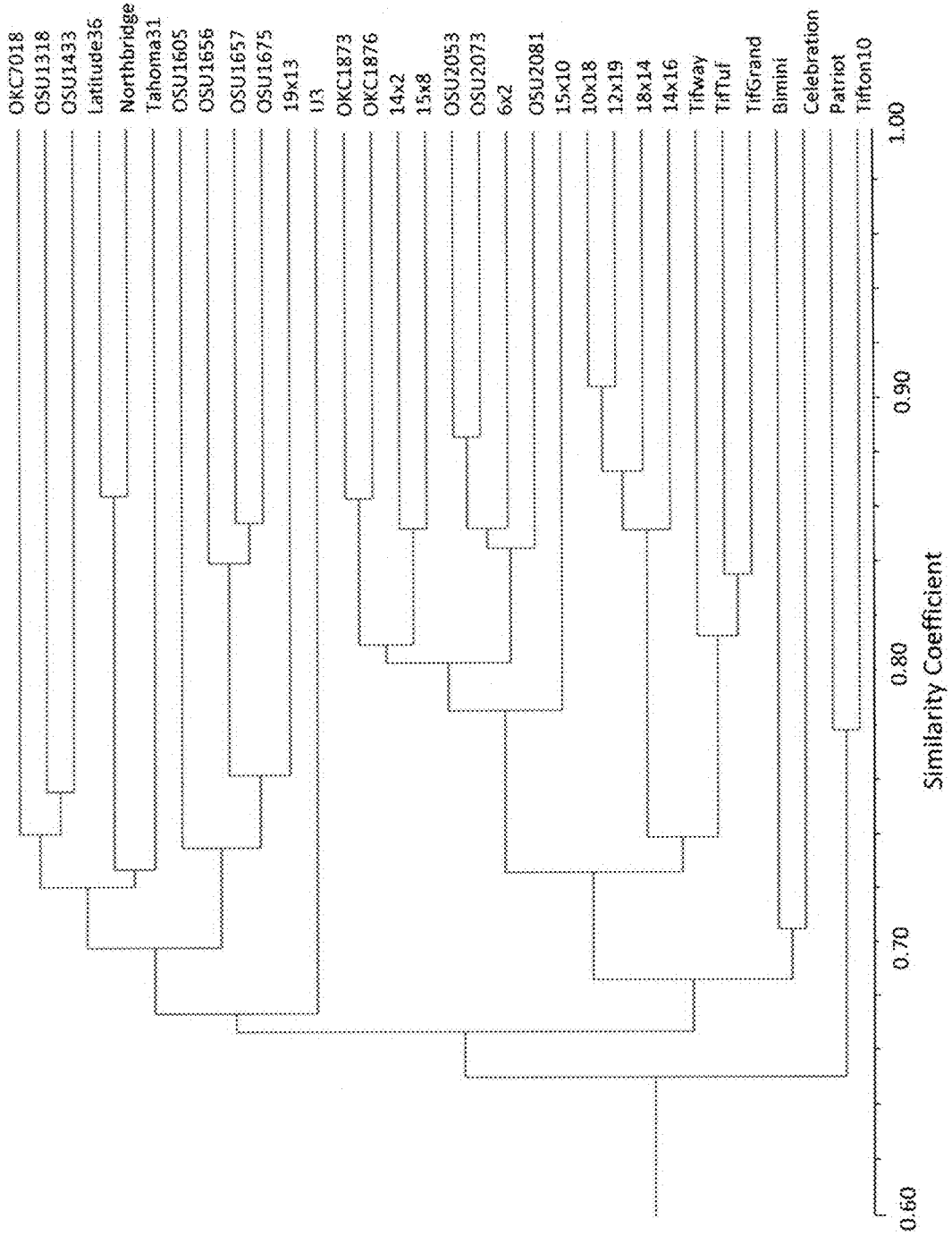
FIG. 1 is a cluster tree of 21 bermudagrass experimental selections and 11 commercial cultivars based on Jaccard similarity coefficients generated from 52 simple sequence repeat markers (SSRs).
Figure 2:
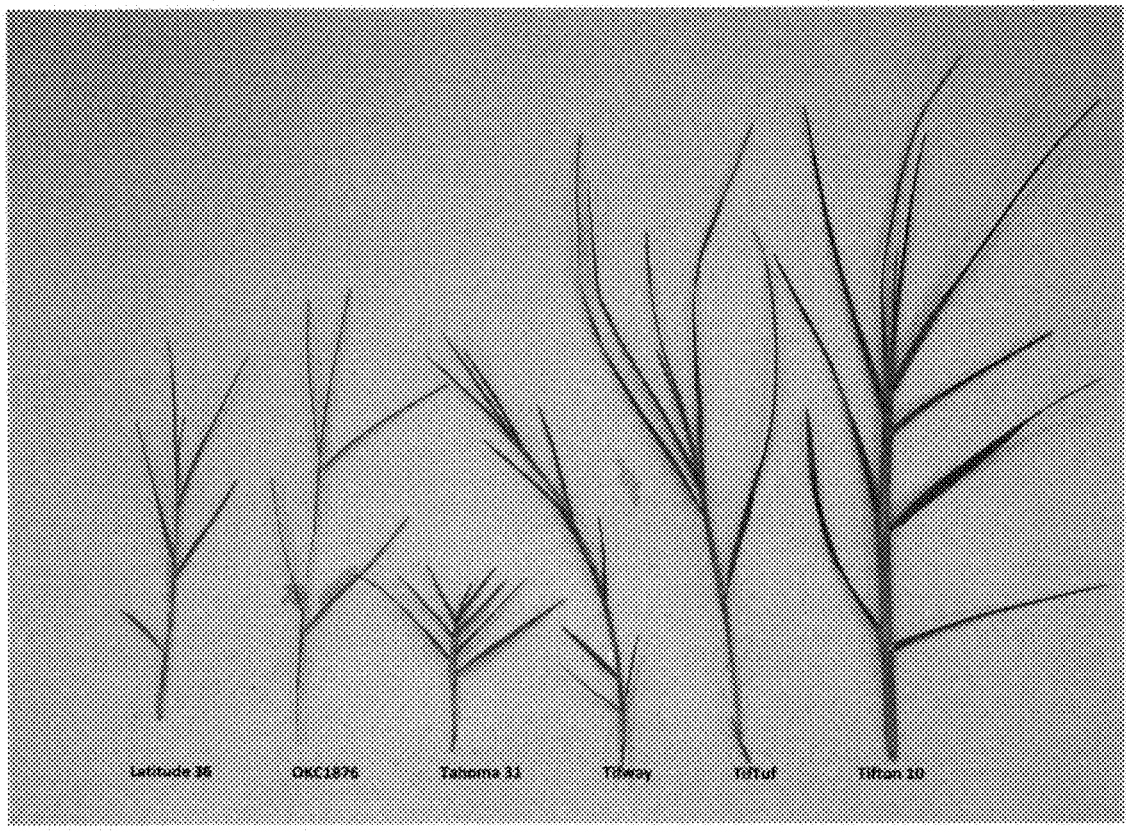
FIG. 2 is a photograph comparing stems and leaves of 'OKC1876', 'Latitude 36', 'Tahoma 31', 'Tifway', 'TifTuf', and 'Tifton 10' grown in an established, replicated nursery in Stillwater, Oklahoma in 2022.
Figure 3:
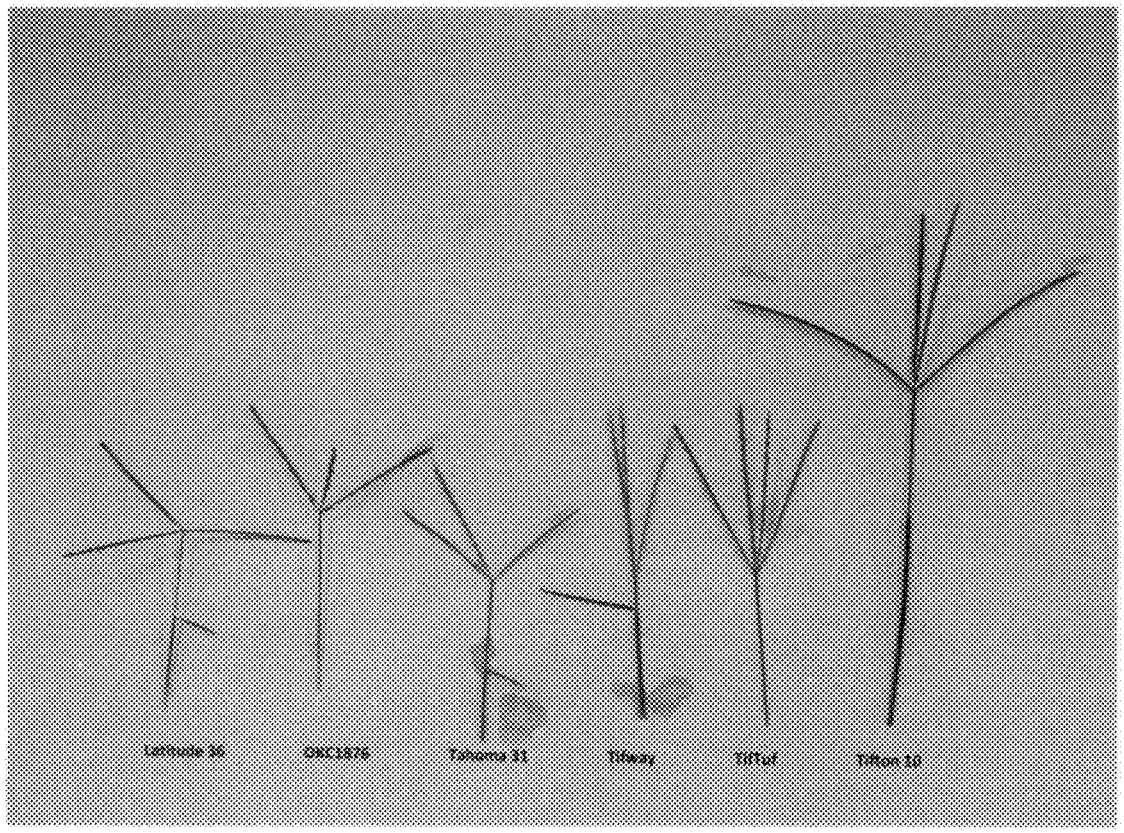
FIG. 3 is a photograph comparing seedheads of 'OKC1876', 'Latitude 36', 'Tahoma 31', 'Tifway', 'TifTuf', and 'Tifton 10' grown in an established, replicated nursery in Stillwater, Oklahoma in 2022

'OKC1876' is a clonally propagated F1 hybrid derived from a cross of female parent *C. transvaalensis* Oklahoma State University (OSU) selection '1115' (unpatented) (2n=2x=18) x male parent *C. dactylon* var. *dactylon* accession 'A12409' (unpatented) (2n=4x=36). A simple sequence repeat marker DNA profiling experiment definitively indicated that 'OKC1876' is a unique genotype, distinct from 11 popular cultivars tested (FIG. 1). 'OKC1876' is sexually sterile, whereas '1115' and 'A12409' are sexually fertile. 'OKC1876' has finer leaf blades than male parent 'A12409' but coarser leaf blades than female parent '1115'.

A small crossing plot was established by planting clonal plants of the two parents in close proximity in Stillwater, Oklahoma in summer 2018. Seed was hand-harvested from the parents in the crossing block in fall 2018. Seedlings from the harvested seed of this cross along with seedlings from other crosses were screened for leaf texture and color, and rooting potential in the spring of 2019. 'OKC1876' was then advanced to the 2019 National Turfgrass Evaluation Program (NTEP) National Bermudagrass Test.

'OKC1876' is sterile and must be propagated vegetatively. It has been clonally propagated through many seasons in Stillwater, Oklahoma. The cultivar is stable, with advanced generation clonal plants appearing identical to the original plant in morphological phenotype and in genetic characteristics that have been measured.

Morphological Characteristics and Performance

'OKC1876' forms a dense turf through its growth of stolons and shoots. It is a perennial grass with vigorous growth in the summer and dormancy in the winter. As it is sexually sterile, its reproduction is solely clonal or vegetative. 'OKC1876' has a foliage color of strong yellow green (corresponds to RHS 144A, The Royal Horticultural Society Colour Chart, $6^{th}$ edition (2015)).

'OKC1876' has a flat, linear leaf blade with a sharp apex. There are sparse silver hairs on the upper leaf blade surfaces, but the lower leaf blade surfaces are smooth. Both sides of the leaf blade surface have olive green color (RHS 137A) in the summer. Leaf blade color in the winter is RHS 8D. The outside surface of the leaf sheath is soft and shiny with sparse fine hairs. The leaf sheath is overlapped at the base but split toward the blade. Leaf sheaths and culm have olive green color (RHS 137A) The leaf texture is soft with a smooth leaf blade margin. The ligule is membranous with short hairs. The cultivar has fine and shallow rhizomes with pale yellow color (RHS 162D), and fine stolons of light olive color (RHS 152A). Collars are white (close to RHS 157D) and continuous, but narrow. When mature, glumes, lemmas, and paleas are brown with a purple color. The auricle is absent with white hairs about 1-2 mm in length. One dormant bud is present and covered by a leaf sheath on a mature node. Leaves are rolled in the bud.

The leaf blade measures 1.9 mm wide and 50.9 mm long on average. The average internode length is 32.3 mm and the average stolon diameter is 0.7 mm. On average, the leaf sheath is 22 mm in length, the ligule is 1-2 mm in length, each spikelet is 2 mm in length, the peduncle is 80 mm in length, and plant culms are 210 mm in length.

Each inflorescence consists of 2-3 racemes in one whorl. There are 20-30 spikelets on each raceme. Each spikelet contains one floret. In Stillwater, Oklahoma, the cultivar flowers in June. 'OKC1876' has yellowish anthers and purple feathery stigmas. Because the cultivar is sterile, it does not produce seed.

'OKC1876' has been evaluated in Stillwater, Oklahoma and more extensively in the 2019 NTEP National Bermudagrass Test. This NTEP test provided data from 8 locations in 2019 and 19 locations in 2020. 'OKC 1119' (U.S. Plant Pat. No. 24,271) [source material Latitude 36® bermudagrass], 'Tifway' (unpatented), and 'DT-1' (U.S. Plant Pat. No. 27,392) [source material TifTuf® bermudagrass] were standard cultivars for vegetatively propagated entries in the national test. The major performance characteristics of 'OKC1876' relative to the national standards are described as follows.

Turfgrass Quality (TQ): TQ in this NTEP test was visually evaluated using a scale of 1 (least quality) to 9 (maximum quality). In 2019, the NTEP test reported TQ ratings at three locations (California, Indiana, and Missouri). In California, 'OKC1876' had a TQ rating (6.2, LSD0.05=0.8) not different from DT-1 (5.8), but better than 'OKC1119' (4.8) and 'Tifway' (4.3). In Indiana, 'OKC1876' had a better TQ rating (7.8, LSD0.05=0.7) than 'DT-1' (7.0), but was not different from 'OKC1119' (7.8) and 'Tifway' (7.3). In Missouri, 'OKC1876's' TQ rating (6.2, LSD0.05=1.2) was better than that of 'Tifway' (4.8), but similar to that of 'DT-1' (6.8) and 'OKC1119' (6.2).

The NTEP test reported 2020 TQ data under management conditions without stress in 13 locations (Virginia, Indiana, Arkansas, Kansas, Missouri, Oklahoma, New Mexico, Florida (Fort Lauderdale and Jay), Tennessee, Kentucky, Alabama, and Mississippi). At each of the sites, the TQ rating of 'OKC1876' was not different from that of 'OKC1119', 'DT-1', and 'Tifway'.

The NTEP test also reported 2020 TQ data under management conditions with stress. Under shade stress conditions in Texas, the TQ rating of 'OKC1876' was not different from that of 'OKC1119', 'DT-1', and 'Tifway'. In the salinity test in New Mexico, the TQ rating of 'OKC1876' was not different from that of the three standard cultivars. In Oklahoma, the 2020 divot recovery rating of 'OKC1876' was statistically not different from that of the three standard cultivars.

When all of the NTEP 2020 TQ data were summarized, 'OKC1876' TQ ranked No. 2 and tied with 'DT-1', followed by 'OKC1119' (No. 6) and 'Tifway' (No. 13). The overall TQ ratings of 'OKC1876' and 'DT-1' were 6.4 (LSD0.05=0.2), statistically not different from 'OKC1119' (6.3), but better than 'Tifway' (6.0). The data summary is presented in Table 1.

TABLE 1

Summary of 2020 turfgrass quality ratings for bermudagrass cultivars in the 2019 NTEP national bermudagrass test.

| Name | Quality mean | Maximum in top 25% |
|---|---|---|
| OKC1131 | 6.5 | 69.2 |
| FB 1628 | 6.4 | 53.8 |
| MSB-1017 | 6.4 | 53.8 |
| OKC1876 | 6.4 | 53.8 |
| DT-1 | 6.4 | 84.6 |
| OKC1119 | 6.3 | 30.8 |
| JSC 2013-10S | 6.2 | 23.1 |
| MSB-1042 | 6.2 | 46.2 |
| OKC1873 | 6.2 | 38.5 |
| RIVIERA | 6.2 | 30.8 |
| ASTRO | 6.1 | 30.8 |
| JSC 2013-12S | 6.1 | 15.4 |
| JSC 2013-8S | 6.1 | 30.8 |
| MONACO | 6.1 | 15.4 |
| MSB-1026 | 6.1 | 38.5 |
| MSB-1050 | 6.1 | 30.8 |
| FB 1630 | 6.0 | 15.4 |
| JSC 2013-5S | 6.0 | 15.4 |
| JSC 2013-7S | 6.0 | 15.4 |
| OKS2015-3 | 6.0 | 15.4 |
| TIFWAY | 6.0 | 23.1 |
| MSB-1048 | 5.9 | 0.0 |

TABLE 1-continued

Summary of 2020 turfgrass quality ratings for bermudagrass cultivars in the 2019 NTEP national bermudagrass test.

| Name | Quality mean | Maximum in top 25% |
|---|---|---|
| JSC 77V | 5.8 | 23.1 |
| JSC 80V | 5.8 | 0.0 |
| OKS2015-7 | 5.8 | 0.0 |
| OKC1406 | 5.7 | 7.7 |
| OKS2015-1 | 5.7 | 7.7 |
| OKC1682 | 5.6 | 0.0 |
| DLF-460/3048 | 5.5 | 0.0 |
| FB 1903 | 5.5 | 15.4 |
| OKC1666 | 5.5 | 15.4 |
| SUN QUEEN (PST-R6MM) | 5.5 | 7.7 |
| FB 1902 | 5.3 | 0.0 |
| PST-R6TM | 5.3 | 7.7 |
| MSB-1075 | 5.1 | 15.4 |
| LSD VALUE | 0.2 | |
| C.V. (%) | 8.7 | |

Drought Resistance: Under drought stress in California, the 2020 NTEP test TQ rating of 'OKC1876' (6.3, LSD0.05=0.5) was not different from that of 'DT-1' (6.5), but significantly better than that of 'Tifway' (5.5) and 'OKC 1119' (4.9). 'DT-1' has been considered a drought resistant standard cultivar in the turf industry and 'OKC1876' exhibits similar drought resistance. In the drought stress test in Texas, the TQ rating of 'OKC1876' (6.2, LSD0.05=1.5) was statistically not different from that of 'DT-1' (6.9), 'OKC 1119' (6.2), and 'Tifway' (6.1).

One NTEP field-based experiment was conducted to measure water use rate in Perkins, Oklahoma. The study consisted of 14 bermudagrass entries, including 'OKC1876' as a local entry (Table 2). The experiment was established in a randomized completed block design with three replicates in 2019. Before water use data were collected in the summers of 2020 and 2021, a rainout shelter was placed over the plots. One inch of water was applied when turfgrass leaf firing in the plot reached 25% during a dry-down period of 65 days in 2020 and 30 days in 2021. In the two dry-down periods, 'OKC1876' was in the top group, requiring the least water (Table 2). The 2020 top group (lowest water use) included 'DT-1', 'OKC1876', and 'FB1682', while the 2021 top group consisted of 'DT-1', 'OKC1876', 'FB1682', and 'OKC1131' (U.S. Plant Pat. No. 31,695) [source material Tahoma 31® Bermudagrass].

TABLE 2

Water applied to bermudagrass entries during the 65-day dry-down period (July 15 to September 16) in 2020 and 30-day dry-down period (July 14 to August 11) in 2021. The same letters in the same column indicate no significant difference.

| Entry | 2020 water use (in inches) | 2021 water use (in inches) |
|---|---|---|
| Dog Tuff | 6.33 a | 2.0 ab |
| OKC1221 | 5.33 ab | 2.0 ab |
| Premier (U.S. Plant Pat. No. 18,247) | 5.33 ab | 2.67 a |
| ASC119 | 4.67 b | 1.67 ab |
| Monaco | 2.67 c | 2.0 ab |
| Tifway | 2.67 c | 0.33 cd |
| ASC118 | 2.67 c | 1.33 bc |
| OSU1896 | 2.33 cd | 1.33 bc |
| JSC2009 | 2.33 cd | 1.33 bc |

TABLE 2-continued

Water applied to bermudagrass entries during the 65-day dry-down period (July 15 to September 16) in 2020 and 30-day dry-down period (July 14 to August 11) in 2021. The same letters in the same column indicate no significant difference.

| Entry | 2020 water use (in inches) | 2021 water use (in inches) |
|---|---|---|
| OSU1646 | 2.00 cde | 2.33 ab |
| OKC1131 | 1.33 def | 0.33 cd |
| FB1628 | 1.00 efg | 0 d |
| OKC1876 | 0.33 fg | 0 d |
| DT-1 | 0 g | 0 d |
| $LSD_{0.05}$ | 1.27 | 1.15 |

Traffic tolerance: The NTEP test reported that under traffic stress in North Carolina, 'OKC1876' had a TQ rating (4.5, LSD0.05=1.2) lower than that of 'DT-1' (5.8), but not different from that of 'OKC1131' (5.3) and 'Tifway' (3.8) in 2020.

A replicated field trial was conducted to evaluate nine commercially available and 87 experimental bermudagrasses for fall traffic tolerance in Oklahoma in 2019 and 2020. Results of the study indicated that 'OKC1876' performed well under traffic stress. In both years, 'OKC1876' had mean percent green cover (PGC) values in the top group, along with varieties 'Bimini' (unpatented), 'Riley's Super Sport'(U.S. Plant Pat. No. 11,181) [source material Celebration® Bermudagrass], 'OKC1119', 'OKC1134' (U.S. Plant Pat. No. 24,116) [source material NorthBridge® Bermudagrass], 'OKC1131', 'DT-1', 'Tifway', and 'U3' (unpatented). Turf performance index (TPI) was used to represent the number of dates out of 14 dates in the two years that an entry was in the top statistical group for PGC. 'OKC1876' had a TPI of 14, the same as 'Bimini', 'Riley's Super Sport', 'OKC1119', 'OKC1134', 'OKC1131', 'DT-1', and 'U3', and higher than that of 'Tifway' (12) and 'Astro' [unpatented] (13). In the study, simple traffic effect (STE) was evaluated to represent the number of dates on which trafficked plots of an entry showed significant reduction in PGC when compared to non-trafficked plots for the given entry out of 14 dates in the two years. 'OKC1876' had an STE of 4 as compared to 'Bimini' (3), 'OKC1134' (3), 'U3' (4), 'Riley's Super Sport' (5), 'OKC1119' (5), 'Astro' (6), 'DT-1' (6), and 'Tifway' (8).

Genetic Color: Genetic color data was collected when the grasses were grown actively without stress and were evaluated using a scale from 1 (light green) to 9 (maximum dark green color). In the NTEP test, the 2020 data indicated that the genetic color rating of 'OKC1876' (6.4, LSD0.05=0.5) over 10 locations was statistically not different from that of 'Tifway' (6.7), 'OKC1119' (6.1), and 'DT-1' (6.0). But, in Alabama, 'OKC1876' had a color rating (7.0, LSD0.05=1.9) significantly better than 'DT-1' (5.0), while no difference from 'Tifway' (6.7) and 'OKC1119' (6.3). In Kansas, 'OKC1876' had a genetic color rating (6.7, LSD0.05=1.0), similar to 'Tifway' (6.3), but better than 'DT-1' (5.3) and 'OKC1119' (5.0).

Fall Color Retention: In the fall season, extended green color retention is a desirable turfgrass trait. Fall color retention is visually assessed using a scale of 1 (brown color) to 9 (full green color). In the NTEP test, 2020 fall color ratings indicated that 'OKC1876' had an outstanding late-season green color. The 2020 September color rating of 'OKC1876' (6.3, $LSD_{0.05}$=2.5) in New Mexico was better than 'DT-1' (3.7), but not different from 'Tifway' (5.3) and 'OKC1119' (5.0). In October, the fall color rating of 'OKC1876' (6.7, $LSD_{005}$=1.6) in Arkansas was better than 'Tifway' (4.3), but similar to 'DT-1' (6.3) and 'OKC1119' (5.3). In Missouri, the October color rating of 'OKC1876' (8.3, $LSD_{0.05}$=1.6) was considerably better than 'Tifway' (3.7) and 'OKC1119' (2.7), but not different from 'DT-1' (8.0). In New Mexico, the October color rating of 'OKC1876' (6.0, $LSD_{0.05}$=2.8) was better than 'DT-1' (3.0), but similar to 'Tifway' (6.3) and 'OKC1119' (6.0). In Virginia, 'OKC1876' had an October color rating (2.7, $LSD_{0.05}$=1.6) less than 'Tifway' (5.0), but similar to 'DT-1' (4.0) and 'OKC1119' (2.0). In November, the fall color rating of 'OKC1876' (6.3, $LSD_{0.05}$=2.9) in New Mexico was better than 'DT-1' (3.0), but not statistically different from 'Tifway' (6.7) and 'OKC1119' (6.0). In Oklahoma, the November color rating of 'OKC 1876' (6.7, $LSD_{0.05}$=0.9) was better than 'OKC1119' (5.7), but not different from 'DT-1' (6.7) and 'Tifway' (6.3).

Leaf Texture: 'OKC1876' has leaf blades of fine texture in the NTEP test. In 2020, the NTEP trial data indicated that the overall mean leaf texture rating (scale 1-9, 9=maximum fine leaf texture) of 'OKC1876' (7.4, LSD0.05=0.3) was statistically the same as that of that of 'DT-1' (7.2) and 'Tifway' (7.1), but better than 'OKC1119' (7.0). The leaf texture ratings of 'OKC1876' in Florida (7.7, LSD0.05=1.0) and Indiana (7.3, LSD0.05=0.8) were better than 'DT-1' (6.3, 6.3), but similar to 'Tifway' (7.0, 7.0), and 'OKC1119' (7.3, 7.3). In Mississippi, the leaf texture rating of 'OKC1876' (7.0, LSD0.05=0.6) was better than the three standard varieties 'DT-1' (6.3), 'Tifway' (6.0), and 'OKC1119' (5.7).

Density: Density is the overall visual effect of the number of living plants per unit area of turfgrass canopy and is evaluated on a 1-9 scale, with 9=maximum density for the species. The 2020 NTEP data indicated that the mean spring density of 'OKC1876' in Oklahoma and Tennessee (6.8, LSD0.05=0.8) was statistically the same as 'OKC1119' (6.0), but better than 'DT-1' (5.3) and 'Tifway' (5.0). The mean summer density rating of 'OKC1876' (6.5, LSD0.05=0.8) in Indiana, Mississippi, Oklahoma, and Tennessee was not different from that of 'DT-1' (7.0), 'Tifway' (6.8), and 'OKC1119' (6.5). The mean fall density rating of 'OKC1876' (5.8, LSD0.05=1.1) in Oklahoma and Tennessee was similar to that of 'DT-1' (6.8) and 'Tifway' (6.9), but smaller than that of 'OKC1119' (7.1).

Spring Greenup: Spring greenup ratings (scale 1-9, 9=maximum greenup) were visually assessed for the earliness of spring regrowth from established plots in the NTEP trial. Spring greenup ratings reflect the comparative winter hardiness of entries as compared to standard cultivars. The 2020 mean spring greenup rating of 'OKC1876' (5.9, LSD0.05=0.7) over nine locations (Alabama, Arkansas, Indiana, Kansas, Kentucky, Mississippi, New Mexico, Oklahoma, and Virginia) was not statistically different from 'OKC1119' (6.4), 'DT-1' (6.4), and 'Tifway' (5.5). In Kansas, 'OKC1876' had a spring greenup rating (5.3, LSD0.05=1.5) lower than 'OKC1119' (7.7), but not different from 'DT-1' (6.3) and 'Tifway' (6.3). In Kentucky and Oklahoma, 'OKC1876' had spring greenup ratings (2.7, LSD0.05=1.5; 1.7, LSD0.05=1.1) lower than 'OKC1119' (5.3, 3.0) and 'DT-1' (5.0, 3.3), but not different from 'Tifway' (2.7, 2.3), respectively. However, in Virginia, 'OKC1876' had a spring greenup rating (6.3, LSD0.05=3.0) better than 'Tifway' (3.0), but not different from 'OKC1119' (5.7) and 'DT-1' (4.7).

Establishment Rate: The NTEP test establishment rate data for 2019 indicates that 'OKC1876' has excellent establishment ratings. In Alabama, Missouri, Mississippi, and New Mexico, 'OKC1876' was not different from the three standard varieties in establishment rate. However, in Florida, 'OKC1876' had an establishment rate (94.5%, LSD0.05=6.2%) faster than 'Tifway' (82.4%), but similar to 'DT-1' (95.4%) and 'OKC1119' (91.8%). In Kansas, the establishment rate of 'OKC1876' (57.8%, LSD0.05=9.7%) was the same as that of 'DT-1' (55.0%) and 'Tifway' (51.1%), but faster than 'OKC1119' (47.7%).

Living Ground Cover (LGC): Living ground cover is visually evaluated using a percentage scale (0-99, 99=complete/maximum live ground cover) in spring, summer, and fall. The NTEP test indicated that 'OKC1876' had very high LGC ratings in 2020, suggesting its overall excellent response to stresses caused by insects, diseases, weeds, and unfavorable environmental factors at the test sites. 'OKC1876' had a mean spring LGC rating in eight locations similar to the three standard cultivars 'DT-1', 'Tifway', and 'OKC1119'. However, 'OKC1876' had summer and fall LGC ratings (95.4, LSD0.05=4.6, three locations; 83.0, LSD0.05=11.3, five locations) similar to 'DT-1' (95.7, 76.1) and 'Tifway' (96.7, 85.5), but better than 'OKC1119' (89.0, 64.3).

Seedhead Ratings: The NTEP test reported seedhead ratings in four locations in 2020. Seedheads are an undesirable trait for turf, generally considered unsightly, and reduce the turf quality. Seedheads are rated from 1 to 9 with 9 equaling no seedheads. In Indiana, 'OKC1876' had a seedhead rating (9.0, LSD0.05=2.1) in 2020 that was better than 'DT-1' (6.0), but not different from 'OKC1119' (8.3) and 'Tifway' (8.3). In Mississippi, the seedhead rating of 'OKC1876' (8.3, LSD0.05=3.1) was better than that of 'OKC1119' (3.0), but similar to 'DT-1' (8.3) and 'Tifway' (6.3). In Kansas and Virginia, the seedhead ratings of 'OKC1876' were not statistically different from that of the three standard cultivars 'Tifway', and 'OKC1119').

Disease Response: Spring dead spot disease incidence (scale 1-9, 9=no disease) reported in Indiana in 2020 indicated that 'OKC1876' had a rating (6.0, LSD0.05=2.4), not statistically different from 'OKC1119' (7.3), 'Tifway' (7.0), and 'DT-1' (6.7).

Insect Response: No significant insect damage was reported on bermudagrass entries including 'OKC1876' in the 2019 NTEP trial.

Sod Tensile Strength and Handling Quality: A replicated field trial was conducted in Oklahoma to test sod tensile strength and sod handling quality. Turf was evaluated using a scale of 1-5, with 1=complete breakage, 3=minimum acceptable, and 5=maximum. The experiment consisted of 16 experimental selections including 'OKC1876' and nine commercial cultivars (Table 3). Results of the test indicated that 'OKC1876' had a sod tensile strength lower than 'Bimini', but similar to 'Astro', 'Riley's Super Sport', 'OKC1119', 'OKC1134','OKC1131', 'DT-1', 'Tifway', and 'U3'. The handling quality of 'OKC1876' was 4.2, which was lower than 'Bimini', but similar to the other eight commercial cultivars.

TABLE 3

Mean sod tensile strength (STS), sod handling quality (SHQ) and shear strength (SS) of 25 bermudagrasses.

| Entry | Sod Tensile Strength Kg $dm^{-2}$ § | Sod Handling Quality (1-5 scale) ‡ |
|---|---|---|
| 18-7-1 | 51 ab | 3.5 a-c |
| 18-7-3 | 33.3 b-d | 3.8 a-c |
| OKC1876 | 33.4 b-d | 4.2 a-c |
| 18-8-4 | 44 a-d | 3.8 a-c |
| 18-8-6 | 28.1 b-d | 3.2 a-c |
| 18-8-7 | 45.5 a-d | 3.7 a-c |
| 18-9-2 | 39.8 b-d | 3.8 a-c |
| 17-4200-19x13 | 31.2 b-d | 3.8 a-c |
| Astro | 37.1 b-d | 2.8 bc |
| Bimini | 69.6 a | 4.5 a |
| Riley's Super Sport | 35.8 b-d | 3.7 a-c |
| OKC1119 | 38.1 b-d | 4.3 ab |
| OKC1134 | 46.5 a-d | 3.8 a-c |
| OSU1117 | 32 b-d | 2.8 bc |
| OSU1337 | 26.2 b-d | 3 a-c |
| OSU1402 | 24.6 b-d | 2.7 c |
| OSU1406 | 24 cd | 2.7 c |
| OSU1628 | 20.5 d | 3 a-c |
| OSU1666 | 20.5 cd | 3 a-c |
| OSU1670 | 21.8 cd | 3.2 a-c |
| OSU1682 | 36.6 b-d | 4.3 ab |
| OKC1131 | 22.4 cd | 3.7 a-c |
| DT-1 | 47 a-c | 3.8 a-c |

TABLE 3-continued

Mean sod tensile strength (STS), sod handling quality (SHQ) and shear strength (SS) of 25 bermudagrasses.

| Entry | Sod Tensile Strength Kg $dm^{-2}$ § | Sod Handling Quality (1-5 scale) ‡ |
|---|---|---|
| Tifway | 37.1 b-d | 3.2 a-c |
| U3 | 31.8 b-d | 3.2 a-c |

† Means within columns followed by same latters are not statistically different at P = 0.05 based on Tukey's HSD test.
§ Sod tensile strength reported in kg $dm^{-2}$ for sod harvested at 1.5 cm depth and 30.5 cm width.
‡ Sod handling quality was measured on a 1 to 5 scale where 1 = complete breakage; 2 = substantial cracking; 3 = moderate cracking; 4 = minimal cracking; and 5 = no cracling.

Major Strengths and Comparative Performance: 'OKC1876' is a new interspecific F1 hybrid turf bermudagrass that exhibits high turfgrass quality, improved drought resistance, excellent fall color retention, reduced seedheads, and wide adaptation in southern states. 'OKC1876' is indicated by available test data to have overall performance equal to or better than current commercial clonal turf bermudagrass cultivars with which it has been compared. It has consistently demonstrated excellent establishment characteristics, fine texture, high turf density, dark green color, good traffic tolerance, and sufficient sod tensile strength for reliable commercial production.

The invention clamed is:

1. A new and distinct Bermudagrass plant named 'OKC1876' substantially as described and illustrated herein.

* * * * *